United States Patent
Gumkowski

(10) Patent No.: US 8,641,423 B2
(45) Date of Patent: Feb. 4, 2014

(54) CIRCUMCISION TESTING AND TRAINING MODEL

(75) Inventor: Emily Gumkowski, Clinton, CT (US)

(73) Assignee: Covidien LP, Mansfield, MA (US)

( * ) Notice: Subject to any disclaimer, the term of this patent is extended or adjusted under 35 U.S.C. 154(b) by 838 days.

(21) Appl. No.: 12/796,296

(22) Filed: Jun. 8, 2010

(65) Prior Publication Data

US 2011/0039241 A1 Feb. 17, 2011

Related U.S. Application Data

(60) Provisional application No. 61/233,874, filed on Aug. 14, 2009.

(51) Int. Cl.
*G09B 23/28* (2006.01)
*G09B 23/30* (2006.01)

(52) U.S. Cl.
USPC .......................................... 434/267; 434/262

(58) Field of Classification Search
USPC ....................................................... 434/267
See application file for complete search history.

(56) References Cited

U.S. PATENT DOCUMENTS

| | | | | |
|---|---|---|---|---|
| 5,074,315 | A | * | 12/1991 | McCuiston ................... 128/844 |
| 7,080,984 | B1 | * | 7/2006 | Cohen .......................... 434/267 |
| 7,303,567 | B1 | | 12/2007 | Smith |
| 2006/0122626 | A1 | | 6/2006 | Duel |
| 2006/0180157 | A1 | * | 8/2006 | Williams ..................... 128/844 |
| 2008/0004631 | A1 | | 1/2008 | Tomlinson |
| 2008/0021482 | A1 | | 1/2008 | Tomlinson |
| 2008/0154283 | A1 | | 6/2008 | Shang |

FOREIGN PATENT DOCUMENTS

CN 200920105375.9 * 2/2009 ............. G09B 23/28

* cited by examiner

*Primary Examiner* — Kathleen Mosser
*Assistant Examiner* — James Hull

(57) ABSTRACT

A model of an adult penis is provided for use in practicing and testing various circumcision procedures. The model includes a form in the approximate shape of an adult penis and a removable and replaceable practice foreskin positionable over the form. The form includes a glans component and a base component. A tube of flexible material is provided to form the artificial foreskin over the glans and base components. A method of forming an practice foreskin for use in testing and training a practitioner in circumcision procedures is also disclosed.

11 Claims, 3 Drawing Sheets

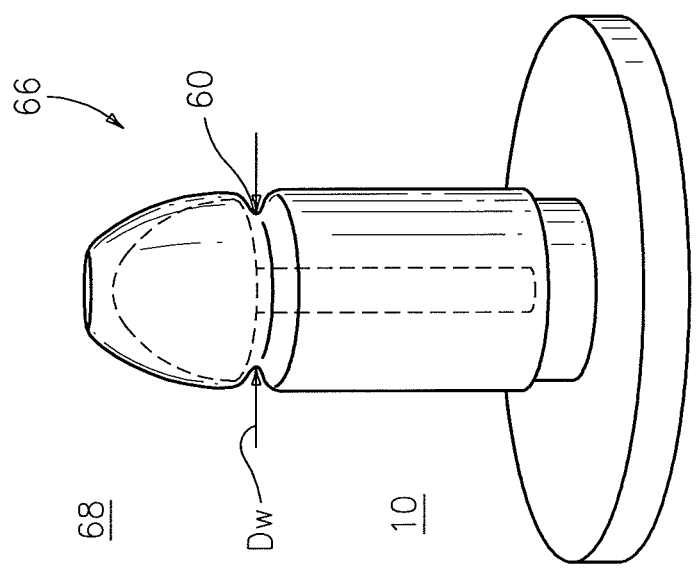
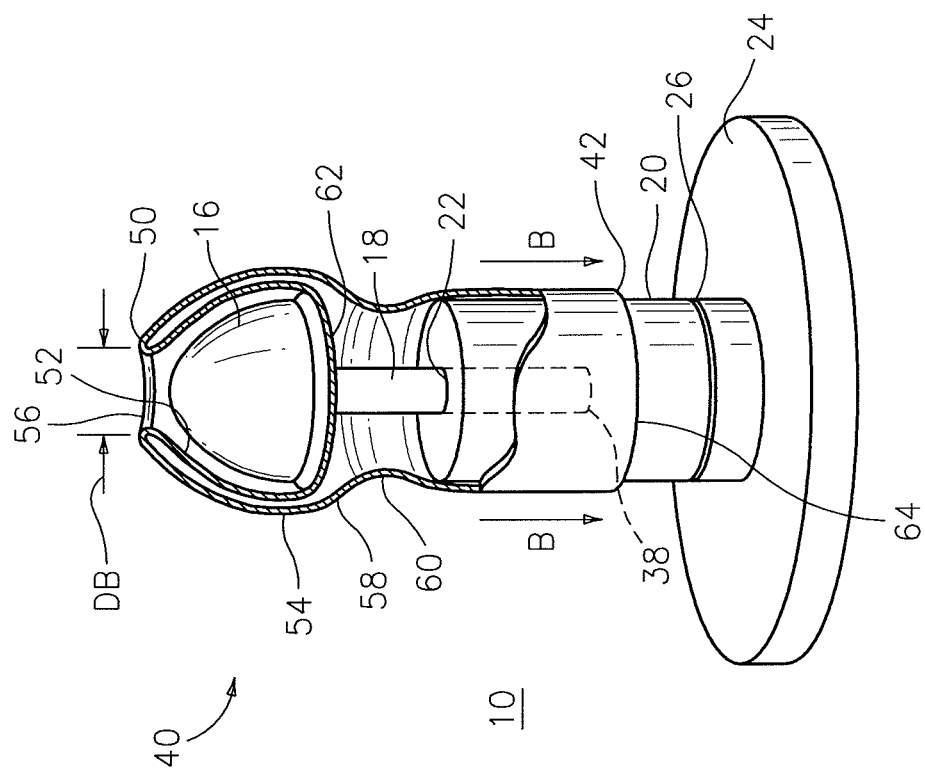

CIRCUMCISION TESTING AND TRAINING MODEL

CROSS REFERENCE TO RELATED APPLICATION

The present application claims the benefit of and priority to U.S. Provisional Application Ser. No. 61/233,874 filed on Aug. 14, 2009, the entire contents of which are incorporated herein by reference.

BACKGROUND

1. Technical Field

The present disclosure relates to a model of an adult penis for use in testing and training a practitioner in various circumcision procedures. More particularly, the present disclosure relates to a model of an adult penis including a form representing the shape of an adult penis and a replaceable tube of flexible material to form an artificial foreskin about the form.

2. Background of Related Art

Circumcision is a surgical procedure in which a section of foreskin, extending over the glans of a penis, is surgically removed at the base of the glans. There are numerous and varying reasons or justifications for performing the circumcision procedure. These reasons may include religious practices, cosmetic desires, health reasons including minimizing the risk of sexually transmitted diseases or "STD's" etc.

Various surgical procedures are available to a surgeon or practitioner in order to perform circumcisions. Most procedures typically include pulling a length of foreskin away from the underlying glans of the penis and severing the foreskin adjacent the base of the glans. A circumcision is a very delicate procedure and care must be taken to properly perform the procedure. While all circumcision procedures require extreme care, when performed upon an adult, the procedure is typically performed with the use of an anesthesia which limits or eliminates the amount of feedback by the patient available to a surgeon or practitioner in the event excess or wrong tissues are being cut.

Many considerations are to be taken into account during the circumcision procedure including proper retraction of the foreskin away from the glans before cutting the tissue. Additionally, care must be taken to cut a foreskin in the proper location in order to avoid damage to underlying vascular tissues and nerves. Further, it is desirable to practice the various aspects of the procedure including maintaining sterile conditions, etc. prior to an actual operation. Unlike many surgical procedures, which can be subsequently performed a second or third time to correct any deficiencies in the initial procedure, circumcisions can typically only be performed once and thus requires a high degree of skill in the practicing surgeon.

Therefore, there is a need for a model of an adult penis for use in testing new circumcision procedures as well as training practitioners in proper circumcision procedures. Further, there is a need for a model of an adult penis having replaceable practice foreskins to allow the practitioner to repeatedly practice the circumcision procedures until the practitioner is comfortable and secure in his skill to properly and safely perform the circumcision procedure on an actual patient.

SUMMARY

There is disclosed a practice foreskin for use in circumcision testing and training. The practice foreskin generally includes a tube having a first section extending in a first direction and having a first end and a second section extending in a second direction and having a second end. A bend is formed between the first section and second section. The first section has a first length extending between the first end and the bend and the second section has a second length extending between the bend and the second end. The second length is at least equal to the first length. The first end has a first opening of a first diameter and the second end has a second opening of a second diameter. The second diameter is greater than the first diameter.

The second section has a waist portion intermediate the bend and the second end. The waist portion has a waist diameter less than the second diameter.

The bend defines a distal opening having an opening diameter less than the second diameter.

The tube is formed of a flexible material. In one embodiment, the flexible material is a synthetic material. In an alternative embodiment, the flexible material is mammalian tissue. In a specific alternative embodiment, the flexible mammalian tissue is a length of tubular organ tissue.

There is also disclosed a method of forming a practice foreskin by providing a length of flexible tubular material and creating a first section having a first open end and extending in a first direction and a second section having a second open end extending in a second direction. The first and second sections are created by forming a bend in the length of flexible tubular material such that the second section is at least a long as the first section.

The bend is formed by everting the second open end of the second section outwardly relative to the first section and drawing the second open end of the second section in the second direction past the first open end of the first section.

A waist is formed in the second section by drawing the second section over an artificial glans, a rod affixed to the artificial glans and a shaft. The artificial glans and shaft have diameters greater than a diameter of the rod such that the second section constricts about the rod to form the waist.

The first open end of the first section is secured about the rod and the second open end of the second section is secured within a recess formed in the shaft.

There is further disclosed a model for circumcision testing and training. The model generally includes a form having a base component and a glans component and a practice foreskin positioned over the form. The base component includes a base and a shaft extending from the base. The shaft defines a bore and the glans component includes an enlarged head and a rod extending from the enlarged head. The rod is removably mounted in the bore of the shaft.

The practice foreskin includes a tube having a first section extending in a first direction and having a first end and a second section extending in a second direction and having a second end. A bend is formed between the first section and second section. The first section has a first length extending between the first end and the bend and the second section has a second length extending between the bend and the second end. The second length is at least equal to the first length.

In a specific embodiment, the shaft has a recess for receipt of the second end of the second section to secure the second section to the shaft.

In one embodiment, the form is formed of a hard, cut resistant material. In a specific embodiment, the form is formed from a ceramic material.

DESCRIPTION OF THE DRAWINGS

An embodiment of the presently disclosed circumcision testing and training model is disclosed herein with reference to the drawings, wherein:

FIG. 5 is a perspective view, partially shown in section, of the circumcision testing and training model during assembly; and FIG. 6 is a perspective view of the assembled circumcision testing and training model.

DETAILED DESCRIPTION OF EMBODIMENT

An embodiment of the presently disclosed circumcision testing and training model will now be described in detail with reference to the drawings wherein like numerals designate identical or corresponding elements in each of the several views. In this disclosure, the term 'proximal" refers to that part or component of the model closer to a body of a "patient", while the term "distal" refers to that part or component of the model further away from the body of the "patient".

Figure 1:
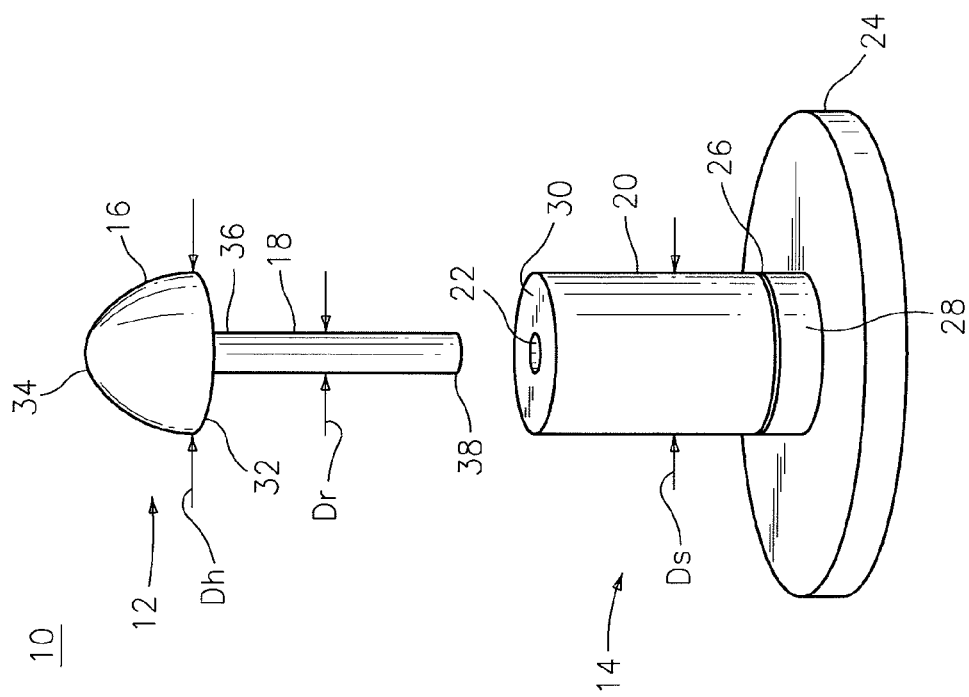
FIG. 1 is a perspective view, with parts separated, of a form of a circumcision testing and training model including a glans component and a base component.

Referring to FIG. 1, there is disclosed a model or form 10 representing an artificial adult penis for use in circumcision testing and training. Form 10 is provided to support a practice skin (as described in more detail hereinbelow) to allow practitioners to practice existing circumcising procedures, as well as, testing new circumcision procedures. Form 10 generally includes a glans component 12 and a base component 14. Glans component 12 is removably mounted on a base component 14. Glans component 12 generally includes an artificial glans or conical head 16 having an elongate rod 18 extending proximally from head 16.

Base component 14 generally includes an elongate shaft 20 having a bore 22 therein for receipt of rod 18. A circular base 24 is provided to stabilize shaft 20 and glans component 12 during use of form 10. A circumferential recess 26 is provided about a proximal end 28 of shaft 20 to secure one end of an artificial foreskin as described in more detail hereinbelow. Bore 22 is formed through a distal face 30 of shaft 20.

Head 16 has a proximal end 32 and a distal end 34. A distal end 36 of rod 18 is affixed to proximal end 32 of head 16. Alternatively, rod 18 may be formed integrally with head 16. A proximal end 38 of rod 18 is insertable into bore 22 formed in distal face 30 of shaft 20.

Head 16 has a maximum diameter Dh at proximal end 32 while rod 18 has a diameter Dr less than diameter Dh of head 16. Shaft 20 has a constant diameter of Ds.

Form 10, including glans component 12 and base component 14, are formed from a substantially hard, inflexible material so as to resist cutting or nicking when engaged by the blades of a surgical instrument. In a specific embodiment, glans component 12 and/or base component 14 are formed from a ceramic material to prevent cutting or nicking which would damage an artificial foreskin used with form 10.

Figure 2:
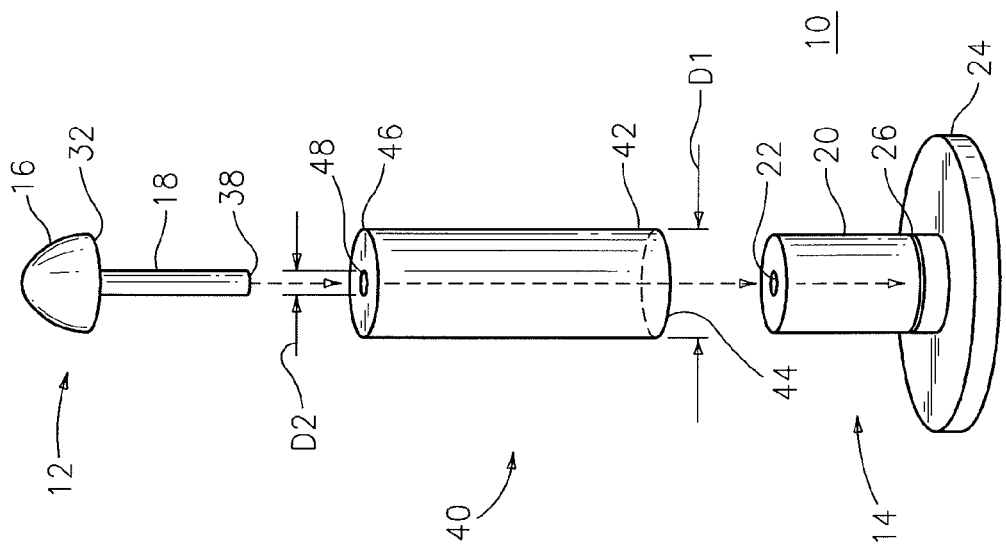
FIG. 2 is a perspective view, with parts separated, of the circumcision testing and training model.

Referring now to FIG. 2, a length of material or tube 40 is provided to be formed into a practice foreskin for use with form 10. Tube 40 includes a first open end 42 defining a first opening 44 and a second open end 46 defining a second opening 48. First opening 44 has a diameter D1 and second opening 48 has a diameter D2 substantially less than diameter D1. Diameter D1 is less than diameters Dh and Ds of proximal end 32 of head 16 and shaft 20, respectively, such that, on assembly, tube 40 is stretched over head 16 and shaft 20. Diameter D2 of second opening 48 is sized to receive rod 18 of glans component 12. It should be noted that tube 20 may initially have a uniform diameter and second open end 46 can be formed by closing second open end 46 through molding, purse stringing, etc. to form second opening 48.

Tube 40 may be formed from various flexible materials including synthetic materials such as, for example, foam material, rubber material, polymeric materials, etc. Alternatively, tube 40 may be obtained through the use of harvested mammalian tissues. These mammalian tissues can provide a more realistic practice material. For example, mammalian tissues mimic the non-uniform thicknesses of a human foreskin. Additionally, the resistance encountered on cutting these mammalian tissues more closely represents that encountered when performing an actual circumcision procedure on a patient. Mammalian tissues may be acquired from various sources such as, for example, tubular organs obtained from various animals such as, for example, pigs, cattle, sheep, etc.

Figure 4:
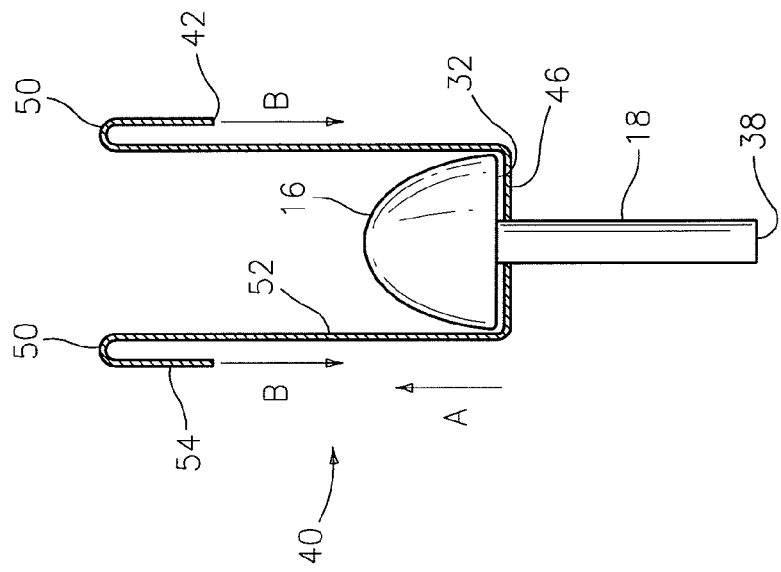
FIG. 4 is a side view, partially shown in section, of the practice skin being everted over the glans component of the circumcision training and testing model of FIG. 2.
Figure 3:
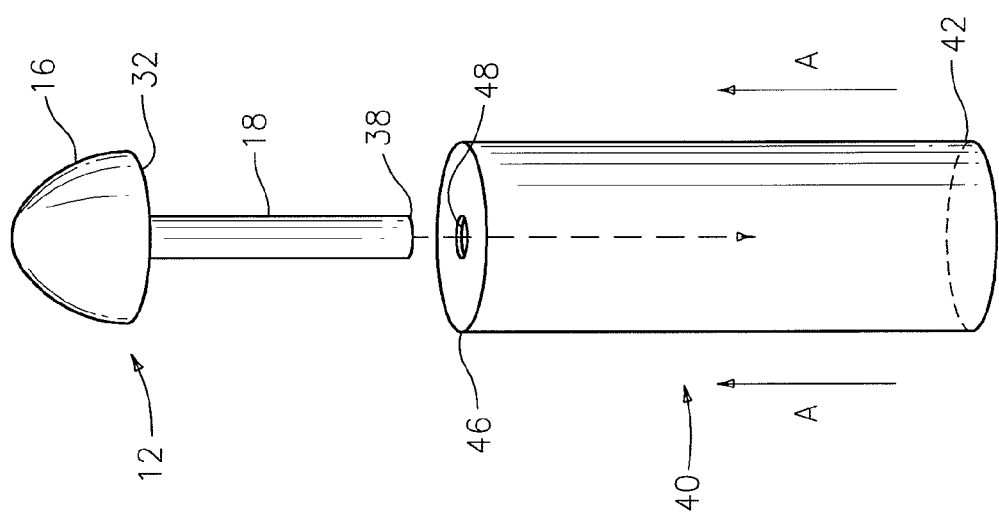
FIG. 3 is a perspective view of a glans component of the form and a practice skin of the circumcision testing and training model of FIG. 2.

Referring now to FIGS. 3-5, the manipulation of tube 40 about form 10 to form a practice foreskin will now be described. Initially, with regard to FIG. 3, proximal end 38 of rod 18 is inserted into second opening 48 in second opened end 46 of tube 40. Proximal end 38 is advanced through second opening 48 until proximal end 32 of head 16 is adjacent or engages second opened end 46 of tube 40.

With reference to FIGS. 3 and 4, next, first open end 42 is everted or flared outwardly and drawn distally in a first direction "A" back over head 16 of glans component 12. Thereafter, with specific reference to FIG. 4, first open end 42 is again everted a second time back over itself in a second direction "B", opposite first direction "A", to form a bend 50. At this point, tube 40 now includes a first section 52 and a second section 54 separated by bend 50.

With continued reference to FIG. 4 and with reference to FIG. 5, at this point, glans component 12 is assembled to base component 14 by inserting proximal end 38 of rod 18 into bore 22 formed in shaft 20 (FIG. 5). As proximal end 38 of rod 18 is inserted through bore 22 and shaft 20, head 16 is approximated toward distal face 30 of shaft 20. First open end 42 of tube 40 is drawn along shaft 20 in the second direction B. Bend 50 defines a bend opening 56 having a diameter DB which is substantially less than diameter Dh of proximal end 32 and 16.

Since tube 40 is formed of a flexible or stretchable material, tube 40 constricts at a center portion 58 to form a waist 60 between a head 16 and shaft 20 and adjacent rod 18.

With reference to FIGS. 5 and 6, first open end 42 of tube 40 continues to be drawn in the second direction B until first open end 42 engages and is received within recess 26 formed in shaft 20. Engagement of first open end 42 within recess 26 secures second section 54 to shaft 20. As best shown in FIG. 5, first section 52 of tube 40 has a length substantially less than the length of second section 54 of tube 40. First section 52 has a final first open end 62 and second section 54 has a final second open end 64 having a diameter greater that the diameter of final first open end 62.

Referring to FIG. 6, upon completion of assembly of tube 40 to form 10, tube 40 is formed into a practice foreskin 66 for use in testing and training of circumcision procedures. Waist 60 has a diameter Dw which is slightly less than diameter Ds of shaft 20 (FIG. 1) to form and undercut mimicking the shape of head 16 of glans component 12. Practice foreskin 66 is now assembled on form 10 and in condition to be operated on by a practitioner. Practice foreskin 66 and form 10 combined to form a model 68 of an adult male penis for practicing and testing circumcision procedures. As noted hereinabove, tube 40, used to form practice foreskin 66, is replaceable by subsequent tubes 40. Model 68 may be provided as a kit including form 10 and multiple tubes 40 to repeatedly practice and test circumcision procedures by a practitioner. Thus, model 68 provides a novel and useful device for allowing a practitioner to practice and test circumcision procedures prior to actual operation upon a patient.

It will be understood that various modifications may be made to the embodiments disclosed herein. For example, the disclosed glans component and base component may be provided as a unitary structure resembling an adult penis. Further, the disclosed practice foreskin may be formed of the alternative materials including various mesh materials, self sealing or healing materials, etc. Additionally, dyes may be incorporated into the spaces defined between the practice foreskin and the form to mimic the presence of blood within the disclosed model. Therefore, the above description should not be construed as limiting, but merely as exemplifications of particular embodiments. Those skilled in the art will envision other modifications within the scope and spirit of the claims appended hereto.

The invention claimed is:

1. A method of forming a practice foreskin comprising:
   providing a length of flexible tubular material and a form including an artificial glans, a rod affixed to the artificial glans, and a shaft;
   inserting the rod through a first open end of a first section of the flexible tubular material;
   extending the first section in a first direction over the artificial glans;
   extending a second section of the flexible tubular member having a second open end in a second direction by forming a bend in the length of flexible tubular material such that the second section is at least as long as the first section; and
   inserting the rod into the shaft.

2. The method as recited in claim 1, wherein the flexible tubular material is a synthetic material.

3. The method as recited in claim 1, wherein the flexible tubular material is mammalian tissue.

4. The method as recited in claim 3, wherein the flexible mammalian tissue is a length of tubular organ tissue.

5. The method as recited in claim 1, wherein the bend is formed by everting the second open end of the second section outwardly relative to the first section and drawing the second open end of the second section in the second direction past the first open end of the first section.

6. The method as recited in claim 1, further comprising forming a waist in the second section by drawing the second section over the artificial glans, the rod affixed to the artificial glans and the shaft, the artificial glans and shaft having diameters greater than a diameter of the rod such that the second section constricts about the rod.

7. The method as recited in claim 1, further comprising securing the first open end of the first section about the rod.

8. The method as recited in claim 1, further comprising securing the second open end of the second section within a recess formed in the shaft.

9. The method as recited in claim 1, wherein the rod is inserted through the first section of the flexible tubular material until the first open end is adjacent the artificial glans.

10. The method as recited in claim 1, wherein the rod is inserted into a bore of the shaft and the artificial glans is approximated relative to the shaft.

11. The method as recited in claim 1, wherein the rod is removably inserted into the shaft.

* * * * *